US00PP34402P2

(12) United States Plant Patent
Bradford et al.

(10) Patent No.: US PP34,402 P2
(45) Date of Patent: Jul. 5, 2022

(54) NECTARINE TREE NAMED 'PEARLICIOUS XV'

(50) Latin Name: *Prunus persica*
Varietal Denomination: 'Pearlicious XV'

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 17/300,921

(22) Filed: Dec. 17, 2021

(51) Int. Cl.
*A01H 5/08* (2018.01)
*A01H 6/74* (2018.01)

(52) U.S. Cl.
USPC ..... Plt./188
CPC ..... *A01H 6/7454* (2018.05)

(58) Field of Classification Search
USPC ..... Plt./188
CPC ..... A01H 6/7454; A01H 5/08
See application file for complete search history.

(56) References Cited

U.S. PATENT DOCUMENTS

PP18,715 P2 4/2008 Bradford
PP18,778 P2 4/2008 Bradford
PP25,828 P3 8/2015 Bradford

*Primary Examiner* — Keith O. Robinson

(57) ABSTRACT

The present invention relates to a new and distinct variety of nectarine tree, *Prunus persica*, broadly characterized by a medium size, vigorous, hardy, self-fertile, productive and regular bearing tree. The variety blooms during the mid season and requires about 550 chilling hours. The fruit matures under the ecological conditions described in mid to late August, with first picking on Aug. 18, 2021. The fruit is uniform, large in size, sub-acidic and very sweet in flavor, globose with slight asymmetry in shape, clingstone in type, firm in texture, white in flesh color, dark red over greenish yellow background in skin color, and has a sweet tasting kernel.

1 Drawing Sheet

Botanical classification: *Prunus persica.*
Variety denomination: 'PEARLICIOUS XV'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of nectarine tree, which has been denominated varietally as 'Pearlicious XV'.

In 2015 we made a first generation hybridization using 'Majestic Pearl' (U.S. Plant Pat. No. 18,778) nectarine as the selected seed parent and 'Kay Diamond VII' (U.S. Plant Pat. No. 18,715) nectarine as the selected pollen parent. Upon reaching maturity the fruit of this hybridization was gathered, and the seeds were removed, cracked, stratified, germinated, and grown as seedlings on their own root in our greenhouse facility. Upon reaching dormancy we transplanted them to a cultivated area of our experimental orchard located near Le Grand, Calif., in Merced County (San Joaquin Valley). During the fruit evaluation season of 2019 we selected the present variety as a single tree from the group of seedlings described above. Subsequent to origination of the present variety of nectarine tree, we asexually reproduced it by budding and grafting in the experimental orchard described above, and such reproduction of plant and fruit characteristics were true to the original tree in all respects. The reproduction of the variety included the use of 'Nemaguard' (unpatented) rootstock upon which the present variety was compatible and true to type.

The present variety is similar to its seed parent, 'Majestic Pearl' (U.S. Plant Pat. No. 18,778) nectarine by being self-fertile, by blooming in the mid season, and by producing nectarines that are white in flesh color, dark red in primary skin color, clingstone in type, large in size, and firm in texture, but is distinguished therefrom by having globose instead of reniform leaf glands, by having a sweet instead of bitter kernel, and by producing nectarines that have more pale yellow background in skin color, that are somewhat larger in size, that are sweeter in flavor, and that ripen about a month later.

The present variety is similar to its pollen parent, 'Kay Diamond VII' (U.S. Plant Pat. No. 18,715) nectarine by being self-fertile, and by producing nectarines that are large in size, firm in texture, and clingstone in type, but is quite distinguished therefrom by having a sweet instead of bitter kernel, by having globose leaf glands instead of having no glands, and by producing nectarines that are white instead of yellow in flesh color, that are sweeter and sub-acidic instead of acidic in flavor, and that ripen about eighty days later.

The present variety is most similar to 'Pearlicious XVI' (U.S. Plant Pat. No. 25,828) nectarine by being self-fertile, by requiring a similar amount of chilling hours, by blooming in the mid season, by having globose leaf glands, and by producing nectarines that are white in flesh color, that are clingstone in type, that are firm in texture, that are sub-acidic in flavor, and that ripen in August, but is distinguished therefrom by producing nectarines that are slightly larger in size, that are a fuller and darker red in primary skin color, that harvest about five days later, and that have a sweet instead of bitter tasting kernel.

SUMMARY OF VARIETY

In summary, the present nectarine variety is characterized by a medium size, vigorous, hardy, self-fertile, productive and regular bearing tree. The variety blooms during the mid season and requires about 550 chilling hours. The fruit matures under the ecological conditions described in mid to late August, with first picking on Aug. 18, 2021. The fruit is uniform, large in size, sub-acidic and very sweet in flavor, globose with slight asymmetry in shape, clingstone in type, firm in texture, white in flesh color, dark red over greenish yellow background in skin color, and has a sweet tasting kernel.

DRAWING

The accompanying photograph consists of four whole fruits positioned to display the characteristics of the skin color and form, one divided fruit to reveal the flesh and stone, typical leaves, a tip shoot growth, and three insets depicting the flower buds and blossoms as they appear on the tree during the blooming season.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Aug. 23, 2021, on the original tree during its sixth growing season. The blossom and flower descriptions were made the previous blooming season. All major color code designations are by reference to the Inter-Society Color Council, National Bureau of Standards. Common color names are also used occasionally.

PARENTAGE

Seed parent: 'Majestic Pearl' (U.S. Plant Pat. No. 18,778) nectarine.

Pollen parent: 'Kay Diamond VII' (U.S. Plant Pat. No. 18,715) nectarine.

TREE

Size: Medium, reaching and maintaining a height of 11' [3.35 m.] and a spread of 7' [2.13 m.] after six growing seasons utilizing typical dormant pruning.

Vigor: Vigorous, responding about average to irrigation and fertilization. The variety grows about 3' [0.91 m.] of surplus top-growth during the spring and summer. The plant should be grown on a standard commercial rootstock for production purposes.

Growth: Upright and moderately dense.

Form: Central leader.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning usually necessary.

Fertility: Self-fertile.

Bearing: Regular bearer, with no crop failures observed.

Chilling requirement: About 550 hours.

Leaf bud burst: Medium to late, during the end of flowering.

Trunk:

*Size*.—Slender, reaching a maximum diameter of 3½" [89.0 mm.] after the sixth growing season.

*Texture*.—Medium to shaggy.

*Bark color*.—A Light grayish brown [60. l.gy.Br] and Brownish gray [64. brGy] variegation with Grayish yellowish brown [80. gy.yBr] crevices present.

*Lenticels*.—Approximate Number Per Square Inch: 8. Color: Strong yellowish brown [74. s.yBr]. Average Size: ⅜" [9.5 mm.] in length. The width is typically one fourth as much as the length. Shape: Elongated.

Branches:

*Size*.—Slender, diameter of main scaffold is 2½" [63.5 mm.] measured 12" above the first lateral, diameter of lowest lateral is 1¼" [31.8 mm.].

*Texture*.—Smooth to medium on first and second year wood, increasing in roughness with age.

*Color*.—1st Year Wood Topside: Grayish red [19. gy.R]. 1st Year Wood Underside: Brilliant yellow green [116. brill.YG]. Older Wood: A Grayish yellowish brown [80. gy.yBr] and Moderate yellowish brown [77. m.yBr] variegation with Deep yellowish brown [75. deep yBr] crevices present.

*Lenticels*.—Number Per Square Inch: About 35 on second year wood. Color: Strong yellowish brown [74. s.yBr]. Average Size: Small, 1/32" [0.8 mm.] in length. The width is typically one fourth as much as the length. Shape: Elongated.

Leaves:

*Size*.—Large. Average Length: 6¼" [158.8 mm.]. Average Width: 2" [50.8 mm.].

*Arrangement*.—Alternate.

*Thickness*.—Medium.

*Form*.—Elliptical.

*Apex*.—Acuminate.

*Base*.—Acute, with an average base angle of 75 degrees.

*Surface*.—Smooth on both sides.

*Color*.—Dorsal Surface: Moderate olive green [125. m.OlG]. Ventral Surface: Moderate yellow green [120. m.YG].

*Red midvein*.—Absent.

*Margin*.—Finely serrate.

*Venation*.—Pinnately net veined.

*Petiole*.—Average Length: 7/16" [11.1 mm.]. Average Thickness: 1/16" [1.6 mm.]. Color: Moderate yellow green [120. m.YG].

*Stipules*.—Number: 2 per leaf, up to 6 per growing tip. Average Length: ¼" [6.4 mm.]. Color: Vivid yellow green [115. v.YG] becoming Moderate brown [58. m.Br] with age.

*Glands*.—Number: 2 to 4 per leaf. Position: Alternate, first pair is located at the intersection of petiole and base of blade. Form: Globose. Size: Medium, about 1/32" [0.8 mm.] in diameter. Color: Moderate yellow green [120. m.YG] becoming Dark olive brown [96. d.OlBr] with age.

*Leaf buds*.—Pointed.

Flower buds:

*Hardiness*.—Hardy, with respect to central California blooming season.

*Diameter*.—Typically ⅜" [9.5 mm.] 1 week before bloom.

*Length*.—Typically ⅝" [15.9 mm.] 1 week before bloom.

*Form*.—Not appressed.

*Surface*.—Pubescent.

*Tip color*.—Pale purplish pink [252. p.pPk].

Flowers: Perfect, complete, perigynous, usually a single pistil, about thirty stamens, five sepal and petal locations alternately positioned.

*Type*.—Showy, large.

*Average flower diameter*.—1 15/16" [49.2 mm.].

*Average flower depth*.—½" [12.7 mm.] when fully open.

*Number of petals*.—Five, extra petal fragments rarely observed, double blossoms not observed.

*Petal arrangement*.—Overlapping.

*Petal shape*.—Circular to oval.

*Petal margin*.—Entire, wavy with occasional notches.

*Average petal diameter*.—¾" [19.1 mm.].

*Average petal length*.—13/16" [20.6 mm.].

*Petal apex*.—Rounded.

*Petal base*.—Rounded to slightly cordate.

*Petal color*.—Pale purplish pink [252. p.pPk] toward the apex and Moderate purplish pink [250. m.pPk] toward the base on both sides.

*Anthocyanin coloration intensity*.—Slight.

*Anther color*.—Moderate reddish orange [37. m.rO] surrounding a Light yellow [86. l.Y] center at bloom onset.

*Pollen*.—Anthers produce an abundance of Brilliant yellow [83. brill.Y] pollen.

*Stigma color*.—Pale greenish yellow [104. p.gY].

*Stigma position*.—Typically located about ⅛" [3.2 mm.] above the nearby anthers.

*Stamen position*.—Typically located about 1/16" [1.6 mm.] below the petals.

*Average pistil length*.—13/16" [20.6 mm.].

*Average stamen length*.—9/16" [14.3 mm.].

*Ovary*.—Non-pubescent.

*Sepal color*.—Grayish purplish red [262. gy.pR] on the outer surface. The inner surface is a somewhat translucent Pinkish white [9. pkWhite] with both Grayish purplish red [262. gy.pR] and Vivid yellow green [115. v.YG] areas visible.

*Sepal length*.—⅜" [9.5 mm.].

*Sepal width*.—5/16" [7.9 mm.].

*Sepal apex*.—Rounded to elliptical to match the sepal length and width.

*Sepal margin*.—Fairly smooth.

*Sepal outer surface*.—Pubescent.

*Fragrance*.—Moderate in degree with a slight hint of rose.

*Blooming period*.—Medium, blooms at the same time as 'Majestic Pearl' (U.S. Plant Pat. No. 18,778) nectarine.

*Onset of bloom*.—One percent on Feb. 17, 2021.

*Date of full bloom*.—Feb. 28, 2021.

*Duration of bloom*.—One to two weeks, dependent on ambient temperature.

*Bloom density*.—Very heavy.

*Number per cluster*.—1 to 3 with single flowers most common.

FRUIT

Maturity when described: Shipping ripe, Aug. 23, 2021.

Date of first picking: Aug. 18, 2021.

Date of last picking: Sep. 2, 2021.

Size: Uniform, large.

*Average diameter axially*.—3¼" [82.6 mm.].

*Average diameter across suture plane*.—3 7/16" [87.3 mm.].

*Average diameter across cheek plane*.—3¼" [82.6 mm.].

*Typical weight*.—9.9 ounces [282 grams].

Form: Uniform, globose, slightly asymmetrical.

*Longitudinal section form*.—Oval.

*Axial view*.—Round.

Suture: A distinct Very deep red [14. v.deep R] line in a shallow groove extending from the base, along the side, and ending just beyond the pistil point.

*Near the base*.—A very shallow groove.

*Along the side*.—A very shallow groove.

*Near the apex*.—A shallow groove.

Ventral surface: Rounded, lipped toward the apex stronger on one side.

Lips: Unequal.

Cavity: Flaring, circular, suture showing on one side, Light greenish yellow [101. l.gY] stem markings present on most.

*Depth*.—¾" [19.1 mm.].

*Breadth*.—1½" [38.1 mm.].

Base: Truncate.

Apex: Rounded, somewhat cordate when viewed parallel to the suture.

Pistil point: Apical, negligible in length, depressed within the suture.

Stem: Medium.

*Average length*.—⅜" [9.5 mm.].

*Average width*.—3/16" [4.8 mm.].

Skin:

*Thickness*.—Medium.

*Surface*.—Smooth.

*Tenacity*.—Tenacious to the flesh.

*Astringency*.—Non-astringent.

*Tendency to crack*.—None observed.

*Color*.—Very deep red [14. v.deep R] toward the apex and streaking into Moderate red [15. m.R] over a Pale greenish yellow [104. p.gY] background with moderate Light yellow [86. l.Y] freckling toward the apex. The primary red colors cover about sixty percent of the total skin area, and the background color covers about forty percent.

Flesh:

*Color*.—Yellowish white [92. yWhite] with Vivid red [11. v.R] streaking toward the stone.

*Surface of pit cavity*.—Covered with Vivid deep red [14. v.deep R] broken fibers when twisted away from the stone.

*Amygdalin*.—Scarce.

*Juice*.—Moderate, rich.

*Texture*.—Firm, crisp.

*Fibers*.—Few, tender.

*Ripens*.—Fairly even, slightly earlier at the apex.

*Flavor*.—Sub-acidic, very sweet, typically 22 brix.

*Aroma*.—Wanting.

*Eating quality*.—Excellent.

STONE

Type: Clingstone.
Size: Medium.
Form: Oval.
Hilum: Narrow, oval.
Base: Slightly rounded to truncate.
Apex: Acute to rounded.
Sides: Equal.
Tip: Sharp, 1/16" [1.6 mm.] in length.
Surface: Irregularly furrowed toward the apex, pitted toward the base.
Ridges: Jagged.
External color: Vivid dark red [17. v.d.R] when first removed.
Pit wall color when cracked: Light brown [57. l.Br].
Cavity surface color: Strong brown [55. s.Br].
Average pit wall thickness: 1/4" [6.4 mm.].
Average length: 1 1/2" [38.1 mm.].
Average width: 1 1/16" [27.0 mm.].
Average breadth: 7/8" [22.2 mm.].
Tendency to split: None observed.
Kernel:
*Form*.—Oval.
*Skin color*.—Light yellow [86. l.Y].
*Pellicle color*.—Dark brown [59. d.Br].
*Vein color*.—Light olive brown [94. l.OlBr].
*Taste*.—Sweet.
*Viable*.—Yes.
*Average length*.—13/16" [20.6 mm.].
*Average width*.—1/2" [12.7 mm.].
*Amygdalin*.—Scarce.

USE

Market: Fresh market and long distance shipping.
Keeping quality: Good, fruit quality observed to remain in good condition after 17 days in standard cold room at 36° Fahrenheit [2° Celsius].
Shipping quality: Good.
Resistance to insects: Not tested.
Resistance to diseases: Not tested.

OTHER NOTES

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types; and/or varying cultural practices.

We claim:

1. A new and distinct variety of nectarine tree named 'Pearlicious XV', substantially as illustrated and described, that is most similar to 'Pearlicious XVI' (U.S. Plant Pat. No. 25,828) nectarine by being self-fertile, by requiring a similar amount of chilling hours, by blooming in the mid season, by having globose leaf glands, and by producing nectarines that are white in flesh color, that are clingstone in type, that are firm in texture, that are sub-acidic in flavor, and that ripen in August, but is distinguished therefrom by producing nectarines that are slightly larger in size, that are a fuller and darker red in primary skin color, that harvest about five days later, and that have a sweet instead of bitter tasting kernel.

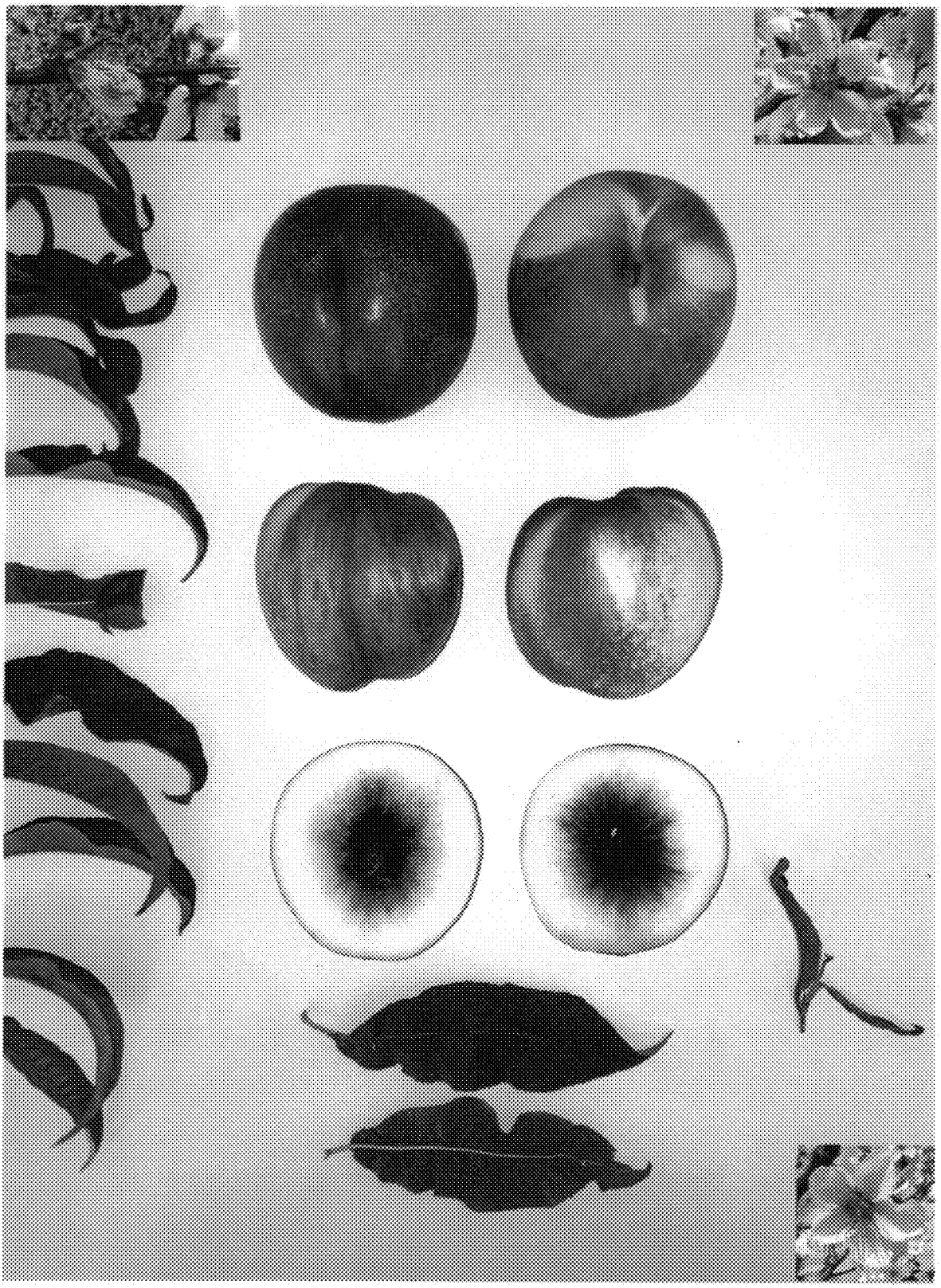

* * * * *